United States Patent [19]
Tanaka et al.

[11] Patent Number: 5,840,510
[45] Date of Patent: Nov. 24, 1998

[54] REAGENT FOR ENDOTOXIN ASSAY AND METHOD FOR ENDOTOXIN ASSAY USING THE SAME

[75] Inventors: Shigenori Tanaka; Hiroshi Tamura, both of Tokyo; Kazuhiro Aita, Fukuoka, all of Japan

[73] Assignee: Seikagaku Kogyo Kabushiki Kaisha (Seikagaku Corporation), Tokyo, Japan

[21] Appl. No.: 885,176

[22] Filed: Jun. 30, 1997

Related U.S. Application Data

[62] Division of Ser. No. 661,705, Jun. 11, 1996, Pat. No. 5,695,948, which is a continuation of Ser. No. 202,177, Feb. 25, 1994, abandoned.

[30] Foreign Application Priority Data

Apr. 26, 1994 [JP] Japan .............................. HEI-5-61464

[51] Int. Cl.$^6$ .............................. C12Q 1/37; C12Q 1/56; C12Q 1/00; C12Q 1/34
[52] U.S. Cl. ................................... 435/23; 435/13; 435/4; 435/18; 435/19; 435/24; 435/29; 435/7.9
[58] Field of Search ................................... 435/23, 13, 4, 435/18, 19, 24, 29, 7.9

[56] References Cited

U.S. PATENT DOCUMENTS

| | | | |
|---|---|---|---|
| 4,188,264 | 2/1980 | Iwanaga et al. | 435/23 |
| 4,273,557 | 6/1981 | Juranas | 435/4 |
| 4,322,217 | 3/1982 | Dikeman | 435/29 |
| 4,495,294 | 1/1985 | Nakahara et al. | |
| 4,510,241 | 4/1985 | Mills | 435/18 |
| 4,717,658 | 1/1988 | Michaels | 435/18 |
| 5,047,353 | 9/1991 | Tsuchiya et al. | |
| 5,059,654 | 10/1991 | Hou et al. | 435/91 |
| 5,085,782 | 2/1992 | Gibson, III et al. | 435/240.2 |
| 5,155,032 | 10/1992 | Tanaka et al. | |
| 5,179,006 | 1/1993 | Matsuura et al. | |
| 5,286,625 | 2/1994 | Tanaka et al. | 435/18 |
| 5,310,657 | 5/1994 | Berzofsky | 435/18 |
| 5,316,911 | 5/1994 | Baek et al. | 435/7.9 |
| 5,695,948 | 12/1997 | Tanaka et al. | 435/23 |

FOREIGN PATENT DOCUMENTS

| | | |
|---|---|---|
| 0500947 | 9/1990 | European Pat. Off. |
| 0426395 | 5/1991 | European Pat. Off. |
| 0507952 | 10/1992 | European Pat. Off. |
| 0513361 | 11/1992 | European Pat. Off. |

OTHER PUBLICATIONS

Sellers et al, *Biochemistry*, 23:5821–5826 (1994).
Roth et al, *J. Biol. Chem.*, 267(23):24097–24102 (1992).
Aoyama et al, *Rinsho Byor*, Abstract, 37(11):1274 (Nov. 1989).
Obayashi et al, *Clinica Chimica Acta*, 149:55–65 (1985).
*Chemical Abstracts*, 103(3):Abstract No. 103:17883h (Jul. 22, 1994).

Primary Examiner—Louise N. Leary
Attorney, Agent, or Firm—Sughrue, Mion, Zinn, Macpeak & Seas, PLLC

[57] ABSTRACT

This invention provides (1) a reagent for endotoxin assay which comprises aprotinin and a limulus amebocyte lysate reagent, (2) a kit for endotoxin assay which comprises the limulus amebocyte lysate reagent and a reagent containing aprotinin, (3) a method for assaying endotoxin in a sample using the limulus amebocyte lysate reagent in which aprotinin is added to the lysate reagent and/or the sample, (4) a method for assaying endotoxin in a serine protease-containing sample using the limulus amebocyte lysate reagent in which the sample is allowed to contact with an aprotinin-immobilized insoluble carrier in advance of endotoxin assay, (5) a carrier for pretreating a serine protease-containing sample on which aprotinin is immobilized, (6) a method for inhibiting factor G activation in which aprotinin is added to the limulus amebocyte lysate reagent and (7) a factor G activation inhibitor which comprises aprotinin as an active ingredient.

Endotoxin assay can be effected based on the factor C system reaction, without influences of factor G contained in the limulus amebocyte lysate reagent and/or serine proteases contained in samples.

6 Claims, 2 Drawing Sheets

REAGENT FOR ENDOTOXIN ASSAY AND METHOD FOR ENDOTOXIN ASSAY USING THE SAME

This is a Divisional of application Ser. No. 08/661,705, filed Jun. 11, 1996 (now U.S. Pat. No. 5,695,948); which in turn is a Continuation of application Ser. No. 08/202,177, filed Feb. 25, 1994 (now abandoned).

FIELD OF THE INVENTION

This invention relates to a reagent for endotoxin assay, a kit for endotoxin assay, a method for endotoxin assay, a carrier for pretreating samples, a method for inhibiting activation of factor G and a factor G activation inhibitor, in which a limulus amebocyte lysate reagent is used.

BACKGROUND OF THE INVENTION

A method for assaying endotoxin (hereinafter referred to as "Et") using a limulus amebocyte lysate (hereinafter simply referred to as "lysate") is well known as a limulus test. The assay comprising the reaction of the lysate is called a limulus reaction. A limulus test has so high sensitivity that is widely employed in pyrogen check of drugs and water, diagnostic use, and the like. The limulus test is based on coagulation of a lysate in the presence of a trace amount of endotoxin. The latest biochemical study has elucidated the fact that the limulus reaction is composed of stepwise activation of several coagulation factors (J. Protein Chem., 5, 255–268 (1986)).

The limulus reaction is illustrated below with respect to a lysate from *Tachypleus tridentatus* by referring to FIG. 1. On endotoxin addition to a lysate, factor C (an endotoxin-sensitive factor; molecular weight: 123,000) in the lysate is activated. The activated factor C limitedly hydrolyzes factor B (molecular weight: 64,000) at a specific site to produce activated factor B. The activated factor B activates proclotting enzyme (molecular weight: 54,000) to convert into clotting enzyme. The clotting enzyme limitedly hydrolyzes coagulogen (coagulant protein; molecular weight: 19,723) at the specific sites in the loop crosslinked by a disulfide linkage, i.e., intermediate between . . . $Arg^{18}$ and $Thr^{19}$ . . . and intermediate between . . . $Arg^{46}$ and $Gly^{47}$ · · · to release peptide C (28 amino acid residues) represented by H—$Thr^{19}$ . . . $Arg^{46}$—OH while converting the remaining part into coagulin gel. Thus, the limulus reaction is composed of a series of reactions (cascade reaction caused by endotoxin is hereinafter referred to as factor C system reaction).

The above-mentioned cascade reaction of a lysate is induced by not only endotoxin but also a (1→3)-β-D-glucan (hereinafter simply referred to as a β-glucan). That is, factor G (a β-glucan-sensitive factor) in FIG. 1 is activated by a β-glucan, the activated factor G converts proclotting enzyme into clotting enzyme, and clotting enzyme acts on coagulogen to produce coagulin gel in the same manner of endotoxin as described above (cascade reaction caused by a β-glucan is hereinafter referred to as factor G system reaction).

The clotting enzyme produced through the cascade reaction is also capable of hydrolyzing an amide linkage of a synthetic peptide substrate separately added to the reaction system, such as t-butoxycarbonyl-leucyl-glycyl-arginine-paranitroanilide (Boc-Leu-Gly-Arg-pNA) to release paranitroaniline. Accordingly, endotoxin or the β-glucan can be quantitatively determined by measuring the absorbance of the thus released paranitroaniline.

Since the generally used lysate contains components concerned in both factor C and factor G system reactions, its use for assaying endotoxin in a sample sometimes entails inaccurate result due to progress of the factor G system reaction triggered by β-glucan possibly contained in the sample.

Thus, the limulus test was proved non-specific for the endotoxin assay, and a number of attempts have been made to develop a method for endotoxin-specific assay. For example, a method has been reported in which endotoxin-specific assay is effected by using a lysate fraction which contains only the factor C system reaction-related components (Obayashi T. et al., *Clin. Chim. Acta*, 149, 55–65 (1985)).

However, this method requires extremely complicated operations for preparing a factor G-free system, including fractionation of a lysate by affinity chromatography using an affinity carrier having immobilized thereon dextran sulfate to eliminate the β-glucan-sensitive factor, i.e., factor G, and reconstruction of factor C, factor B and proclotting enzyme for use in endotoxin-specific assay.

On the other hand, it is known that all of these activated factors involved in the limulus reaction (factor C and factor G system reactions) are serine proteases, and the limulus test results in false positive in the presence of other serine proteases such as trypsin and thrombin which convert coagulogen into coagulin gel through its limited hydrolysis or hydrolyze the above-mentioned synthetic substrate, nevertheless the presence or absence of Et and β-D-glucan (Harada T. et al., *J. Med. Enzymol.*, 3, 43–60 (1978)). In consequence, it is impossible so far to assay endotoxin in serine protease-containing samples by limulus test.

SUMMARY OF THE INVENTION

A first object of the present invention is to specifically assay endotoxin in samples using a lysate reagent, by avoiding influence of β-glucan sensitive factor (factor G) contained in the lysate and thus based on only the factor C system reaction.

A second object of the present invention is to accurately assay endotoxin in serine protease-containing samples using a lysate reagent, by excluding false positive reaction through specific inhibition of the activity of serine proteases in the samples without inhibiting activity of the activated factors involved in the factor C system reaction in the lysate.

With the aim of attaining the first object described above, the present inventors have examined substances capable of selectively inhibiting the factor G system reaction, namely activation of factor G by β-glucan and/or activity of activated factor G, without inhibiting the factor C system reaction in the lysate. As a result, it was found that, among various serine protease inhibitors, an appropriate amount of aprotinin can strongly inhibit the factor G system reaction without substantially inhibiting the factor C system reaction.

Also, with the aim of attaining the second object, the present inventors have examined substances which can inhibit serine proteases in samples selectively without inhibiting the factor C system reaction in the lysate. It was found as a result that serine proteases in samples can be inhibited selectively without inhibiting the factor C system reaction, by carrying out the limulus reaction in the presence of an appropriate amount of aprotinin as one of various serine protease inhibitors or by allowing samples to contact with an appropriate amount of aprotinin in advance of the reaction.

We have examined various serine protease inhibitors such as $\alpha_1$-antitrypsin, antithrombin III, $\alpha_2$-plasmin inhibitor, ovomucoid inhibitor, hirudine, gabexate mesylate and the like, in addition to aprotinin, and found that aprotinin alone can preferentially inhibit the factor G system reaction in the limulus reaction, while other serine protease inhibitors not only inactivate serine proteases in samples but simultaneously inhibits both the factor C system and factor G system reactions thereby inhibiting the entire limulus reaction. The present invention has been accomplished by further developing these findings.

The present invention provides a reagent for endotoxin assay which comprises a limulus amebocyte lysate reagent and aprotinin.

The present invention also provides a kit for endotoxin assay which contains a limulus amebocyte lysate reagent and a reagent containing aprotinin.

The present invention further provides a method for endotoxin assay using a limulus amebocyte lysate reagent, wherein aprotinin is added to the limulus amebocyte lysate reagent and/or a sample.

Specifically, in the above assay method, aprotinin to be added to the limulus amebocyte lysate reagent and/or a sample is used in an amount effective for inhibiting activation of factor G existing in the limulus amebocyte lysate reagent. Further, aprotinin is added to the limulus amebocyte lysate reagent and/or a serin protease-containing sample in an effective amount for inhibiting the serine protease in the sample.

The present invention further provides a method for assaying endotoxin in a serine protease-containing sample using a limulus amebocyte lysate reagent, wherein the sample is allowed to contact with an aprotinin-immobilized insoluble carrier in advance of the assay.

The present invention further provides an insoluble carrier for pretreating a serine protease-containing sample in advance of endotoxin assay using a limulus amebocyte lysate reagent, on which aprotinin is immobilized.

Furthermore, the present invention provides a method for inhibiting factor G activation which comprises adding aprotinin to a limulus amebocyte lysate reagent containing factor G, and a factor G activation inhibitor which comprises aprotinin as an active ingredient capable of inhibiting activation of factor G existing in the limulus amebocyte lysate reagent and a buffer agent for maintaining an optimum pH range for a reaction of factor C with endotoxin.

DETAILED DESCRIPTION OF THE INVENTION

Aprotinin, also called basic pancreatic trypsin inhibitor, is a basic polypeptide consisting of 58 amino acid residues and having an isoelectric point of 10.5 extracted from bovine lung, pancreas or parotid gland, which inhibits various intracellular proteases such as kallikrein, plasmin, trypsin, chymotrypsin and the like. As a pharmaceutical drug, aprotinin is manufactured by Bayer AG under a trade name of Trasylol.

Examples of the limulus amebocyte lysate reagent (hereinafter simply referred to as "lysate reagent") used in the present invention include amebocyte extracts prepared from hemolymph of horseshoe crab, such as *Limulus polyphemus, Tachypleus tridentatus, Tachypleus. gigas, Carcinoscorpius rotundicauda* and the like in the usual way (cf. *J. Biochem.*, 80, 1011–1021 (1976)). To these extracts may be added a divalent metal salt which is effective for the activation of factor C, such as hydrohalide (e.g., chloride), sulfate or the like of an alkaline earth metal (e.g, magnesium, calcium, strontium or the like), a substrate for the clotting enzyme, such as the above-mentioned synthetic substrate, Boc-Leu-Gly-Arg-pNA, and a pH adjusting agent, such as Tris-HCl or the like buffer solution. A commercially available lysate reagent can also be used. The lysate reagent may be in any form such as liquid, powder, solid or the like.

According to the present invention, the lysate reagent containing factor G is preferably used, but those from which factor G has been eliminated or in which factor G was inactivated with an inhibitor other than aprotinin may also be used.

The above-mentioned first object of the present invention can be attained by the endotoxin assay which comprises (A) using a reagent prepared by adding aprotinin to a lysate reagent to inactivate factor G system reaction-related components (hereinafter referred to as "aprotinin-containing lysate reagent" ), (B) adding aprotinin to a sample and assaying the sample using a commonly used lysate reagent so that activation of factor G system reaction-related components in the lysate reagent can be inhibited, or a combined method of (A) and (B) in which aprotinin is added to both the lysate reagent and a sample.

In this instance, though the amount of aprotinin necessary for completely inhibiting the factor G system reaction depends on the type of the lysate reagent, one skilled in the art would easily determine the appropriate amount by the following preliminary experiment.

With cooling on an ice bath, aprotinin (endotoxin-free) is added to a predetermined amount of the lysate reagent in a varied amount, endotoxin-free β-glucan is added thereto in such an amount that it can fully activate the lysate reagent under usual measurement conditions and then the reaction is carried out under the usually used conditions. Under these conditions, the amount of aprotinin which completely inhibit activation of the lysate reagent by β-glucan is determined.

Based on the thus determined amount of aprotinin, a suitable amount of aprotinin where the factor C system reaction proceeds corresponding to the concentration of endotoxin in a sample is determined. The amount of aprotinin to be used is approximately from 5 mg to 500 mg per 1 ml of the lysate reagent.

The above-mentioned second object of the present invention can be attained by the endotoxin assay which comprises (C) allowing aprotinin to react with serine protease in a sample and subsequently allowing the resulting reaction mixture to react with the aprotinin-containing lysate reagent, (D) adding aprotinin to a sample in such an amount that activity of factor G in the lysate reagent can be inhibited, and allowing the sample to react with a lysate reagent, (E) adding aprotinin in advance to the lysate reagent in such an amount that factor G in the lysate reagent can be inhibited as well as serine protease activity in a sample or (F) allowing a serine protease-containing sample to contact in advance with an aprotinin-immobilized insoluble carrier, thereby removing or inactivating the serine protease and subsequently assaying the sample thus treated using the lysate reagent.

It should be noted however that the method (E) can be effected when aprotinin is used within such a range that it does not inhibit the factor C activity.

Also, in the case of the methods (C) to (E), Et assay can be made more accurately and simply using the Et-specific lysate reagent since aprotinin is used in an amount required for inhibiting only serine protease activity and thus the factor C system reaction can be controlled more easily. In that case, it is desirable to eliminate the amount of aprotinin required for inhibiting factor G from the above-mentioned range of aprotinin amount. The amount may not be reduced unless the provided amount is effective for endotoxin assay.

In the case of the methods (C) to (E), the sample may be a serine protease preparation (in other words, the case where the presence of Et in the serine protease preparation is determined) or the sample may be contaminated with a serine protease. In that case, the amount of aprotinin can be determined in the following manner.

In a synthetic substrate method, aprotinin having a varied concentration and a sample are added to the limulus reagent for synthetic substrate method use in which its lysate component is replaced by distilled water, the resulting mixture is incubated at 37° C. to effect the usual limulus reaction and then the amount of aprotinin showing the same value as that of the blank test is determined, which can be used for assaying the sample.

In a gelation method or a turbidity method, aprotinin having a varied concentration and a sample are added to the lysate reagent in which factor C and factor G are removed or inactivated and coagulogen is contained, the resulting mixture is incubated at 37° C. to effect the usual limulus reaction and then the amount of aprotinin showing the same value as that of the blank test is determined. The Et assay can be carried out by adding the thus determined amount of aprotinin to the sample.

In this instance, the above-mentioned amount of aprotinin is a desired value and therefore can be increased slightly within such a range that it does not affect the endotoxin assay.

Though it depends on the type and amount of serine protease contained in the sample, aprotinin may be used in an amount sufficient for completely inhibiting the serine protease contained in the sample and does not substantially interfere with the factor C system reaction. Specifically, aprotinin can be added in general in an amount of approximately from 1 to 2,000 moles per mole of the protease, or approximately from 300 $\mu$g to 10 mg in a practical manner.

In consequence, when a sample to be tested contains a serine protease and the lysate reagent contains factor G, the amount of aprotinin is the sum of those required for inhibiting both factor G and serine protease.

In the case of the method (F), the amount of aprotinin to be immobilized to an insoluble carrier can be determined based on the amount of a serine protease contained in each sample and the like factors, but generally within the range of from 2 to 100 moles per mole of the serine protease. The insoluble carrier is not particularly limited provided that it does not contain Et and can chemically immobilize aprotinin without reducing desired activity. Illustrative examples of such carriers include polyamide compounds, cellulose compounds, agarose compounds, polyacrylamide compounds, dextran compounds, vinyl polymer compounds (porous copolymers with glycidyl methacrylate) and the like. Immobilization of aprotinin may be effected by usually used means such as a method in which formyl groups are introduced into cellulose gel and aprotinin is allowed to bind to the thus treated gel in the presence of NaCNBH$_3$, as well as a diazotization method, a CNBr method, an acid azide method and the like.

The insoluble carrier can be used in any form. It may be molded to the form of the bead, tip, tube, film and the like. Examples of the insoluble carrier include any commercially available carrier for affinity chromatography such as an agarose gel carrier activated by a CNBr method (e.g., Sepharose available from Pharmacia, etc.) and a cellulose carrier having an active group such as formyl groups or carboxyl groups (e.g., Formyl-Cellulofine, Carboxyl-Cellulofine, both available from Seikagaku Corporation, etc.).

In the method (F), a serine protease-containing sample is allowed to contact with an aprotinin-immobilized insoluble carrier, and the resulting unabsorbed solution is used in the assay. During this treatment, it is necessary to take special precautions to prevent contamination by Et. According to the methods (C) to (E), Et can be simply and rapidly assayed with minimum danger of contamination of the sample with Et.

The endotoxin assay methods, such as methods (A) to (E), excluding method (F), can be carried out in the presence of aprotinin, for example, by the following methods (i) to (ix).

(i) A method in which aprotinin is added to amebocyte followed by extraction to serve as an aprotinin-containing lysate reagent for the Et assay.

(ii) A method in which aprotinin is added to the extracted lysate to serve as an aprotinin-containing lysate reagent for the Et assay.

(iii) A method in which a lyophilized lysate reagent preparation is dissolved in an aprotinin-containing solution to serve as an aprotinin-containing lysate reagent for the Et assay.

(iv) A method in which aprotinin is added to a lyophilized lysate reagent preparation dissolved in an appropriate solution to serve as an aprotinin-containing lysate reagent for the Et assay.

(v) A method in which a lyophilized preparation, which is prepared by adding aprotinin to amebocyte followed by extraction and lyophilization or adding a necessary amount of aprotinin to a lysate reagent followed by lyophilization, is dissolved in an appropriate solution to serve as an aprotinin-containing lysate reagent for the Et assay.

(vi) A method in which a lyophilized preparation containing a lysate reagent and a synthetic substrate is dissolved in an aprotinin-containing solution or aprotinin is added to a solution prepared by dissolving the lyophilized preparation in an appropriate solution to serve as an aprotinin-containing lysate reagent for the Et assay.

(vii) A method in which a reagent, which is prepared by adding a necessary amount of aprotinin to a mixed solution of a lysate reagent and a synthetic substrate followed by lyophilization, is dissolved in an appropriate solution to serve as an aprotinin-containing lysate reagent for the Et assay.

(viii) A method in which a necessary amount of aprotinin is added to a sample to be tested.

(ix) A method in which a sample to be tested is added to a lysate reagent, followed by immediately adding aprotinin thereto.

In this instance, the method (viii) may be used alone or together with the methods (i) to (vii).

The solution to be used for dissolving lyophilized preparation in the above methods (iv), (v), (vi) and (vii) is an appropriate buffer capable of stably maintaining components in the lysate reagent involved in factor C system reaction and maintaining an optimum pH range (pH 7.0 to 8.5) for a reaction of factor C with endotoxin. Examples of the solution include water and a buffer solution capable of maintaining the above pH range which contains a buffer agent such as Tris(hydroxymethyl)aminomethane, Tris (hydroxymethyl)-aminomethanemaleate, 1,4-piperazinediethanesulfonate, morpholinopropanesulfonate, N-2-hydroxyethylpiperazine-N'-2-ethanesulfonate, triethanolamine, imidazole and Tris(hydroxymethyl) imidazole. The aprotinin-containing solution used in the above methods (iii) and (vi) is prepared by adding a necessary amount of aprotinin to the above-described solution.

As described above, aprotinin may be used in any optional manner in the Et assay method of the present invention, provided that the factor C system reaction in the lysate reagent can function normally or within a reasonably functionable range and that quantitative or qualitative assay of Et can be made.

Figure 1:
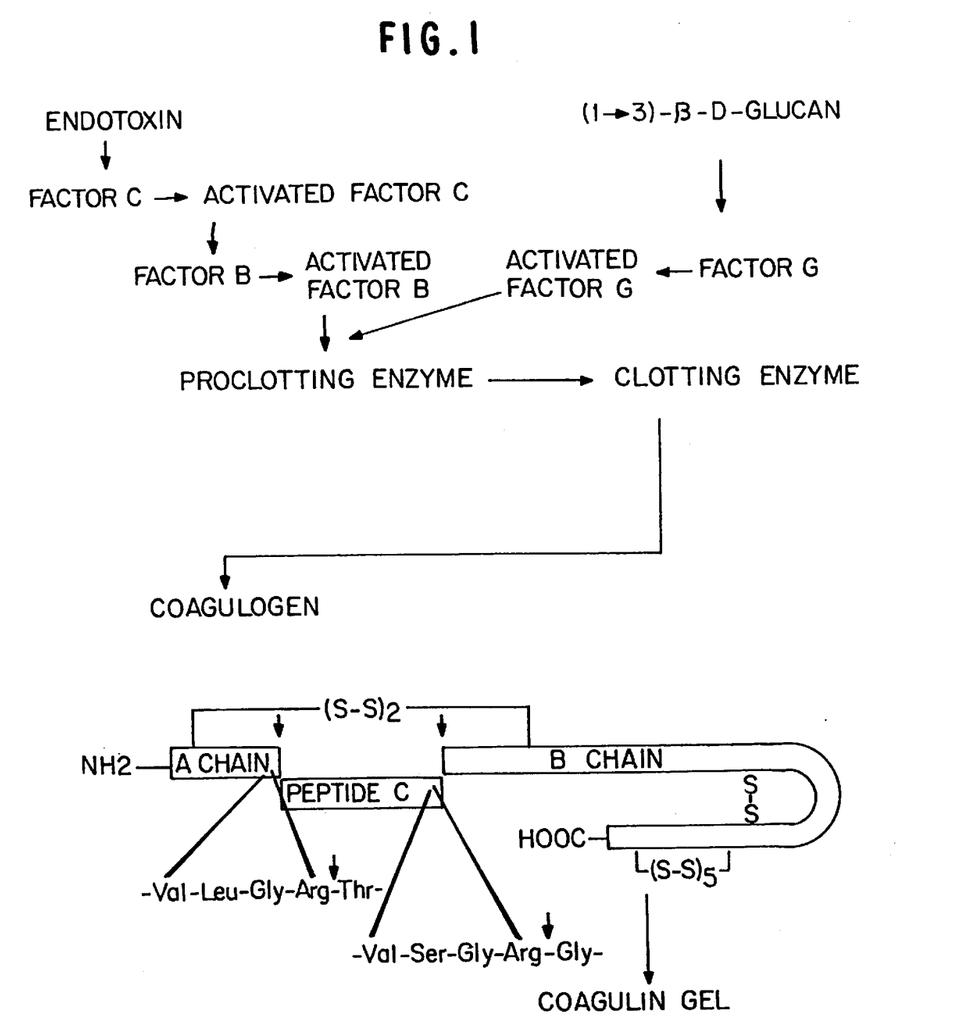
FIG. 1 shows mechanism of limulus reaction.

The endotoxin assay using the reagent of the present invention may be effected in the usual way by determining the activity of clotting enzyme formed by its activation through the cascade reaction shown in FIG. 1.

For the measurement of amidase activity of the clotting enzyme, the above-mentioned synthetic peptide substrate having a chromogenic residue may be used, as well as its analogous synthetic peptide substrate which has the same peptide sequence but the carboxyl group of its C-terminal amino acid is substituted, in place of the above-mentioned chromogenic residue, with a known fluorescence residue, a luminescence residue, ammonia or the like via an amide bond. The amidase activity is determined by measuring the reaction product formed from the synthetic substrate by the action of the clotting enzyme. For example, the above-described synthetic substrate is allowed to coexist with a reaction system which contains the reagent of the present invention and endotoxin, and a dye, a fluorescent substance or ammonia formed by the reaction (cascade reaction and, if necessary, a conversion reaction of the reaction product into other dyes) is detected respectively by a spectrophotometer, a fluorophotometer, a chemi-luminescent detector, an ammonia detection electrode (JP-A-62-148860; the term "JP-A" as used herein means an "unexamined published Japanese patent application) or the like.

Determination of protease activity of the clotting enzyme may be effected by a method in which the clotting enzyme is allowed to react with coagulogen (substrate) which is contained in the reagent of the present invention or added separately, and the resulting gelation of coagulin is measured, for example, by an appropriate instrument such as a turbidity measuring instrument, a viscosity measuring instrument or the like or by the naked eye judgement.

In the practice of the assay of the present invention, it is necessary to use a divalent metal salt effective for the activation of the above-mentioned cascade reaction system. Examples of such divalent metal salts include hydrohalides (chloride) and sulfate of alkaline earth metals such as magnesium, calcium, strontium and the like.

Though these metal salts can be added independently upon the limulus reaction, it is desirable to add the divalent metal salt to the lysate reagent and drying the mixture to solid under a non-heating condition such as lyophilization. The reagent for use in the measurement of amidase activity may preferably be coexisted with the above-mentioned synthetic peptide substrate in addition to the divalent metal salt, which may be further dried.

The endotoxin assay according to the present invention can be carried out more easily and rapidly by using a kit comprising the above-described reagents. The kit of the present invention comprises the lysate reagent and the aprotinin-containing reagent. The aprotinin-containing reagent may further comprise a buffer agent as described above. Specific example of the kit includes:(1) lyophilized lysate reagent and a solution for dissolving it in; (2) lyophilized aprotinin and a solution for dissolving it in; (3) lyophilized standard endotoxin and a solution for dissolving it in; and (4) reagents for synthetic chromogenic substrate method including distilled water for blank test.

Samples to be tested for the Et assay is not particularly limited, and any sample required for the quantitative measurement of Et or confirmation of its presence can be used. Examples of such samples include biological samples, drugs, water for medical use and the like. As described above, the present invention is especially useful for the assay of serine protease-containing samples.

According to the present invention, types of the serine proteases contained in samples to be tested are not particularly limited, provided that their activities are inhibited by aprotinin. Examples of such serine proteases include kallikrein, plasmin, trypsin, chymotrypsin, thrombin and the like.

The following examples are provided to further illustrate the present invention, but are not to be understood to limit the scope of the invention.

EXAMPLE 1

Et Assay Using a Reagent Prepared by Adding Aprotinin to a Lysate Reagent

1) A 1.0 liter portion of hemolymph of *T. tridentatus* was centrifuged at 1,500 rpm at 4° C. for 10 minutes, and about 21 g of the precipitate (amebocytes) thus obtained was mixed with 210 ml of 0.02M Tris-HCl buffer (pH 8.0) and homogenized uniformly in a homogenizer (Polytron R PT10, the trade name of the product manufactured by Kinematica) to effect extraction. The resulting homogenate was subjected to centrifugation at 10,000×G for 30 minutes under ice-cooling to obtain 190 ml of supernatant (lysate reagent).

To 0.04 ml of the thus obtained lysate reagent were added 0.04 ml of 0.5M Tris-HCl/0.4M magnesium sulfate buffer (pH 8.0) containing 0.5, 1.0, 2.0, 4.0 or 6.0 mg of aprotinin and 0.02 ml of 4.0 mM Boc-Leu-Gly-Arg-pNA, thereby obtaining an aprotinin-containing lysate reagent (invention). Separately, to 0.04 ml of the lysate reagent were added 0.04 ml of 0.5M Tris-HCl/0.4M magnesium sulfate buffer (pH 8.0) containing no aprotinin and 0.02 ml of 4.0 mM Boc-Leu-Gly-Arg-pNA. To each of these was added 0.1 ml of distilled water (blank, hereinafter referred to as "DW") or β-glucan (500 ng/ml, prepared by the method described below) as a sample to be tested. After allowing each of the resulting mixtures to react at 37° C. for 30 minutes, the thus formed p-nitroaniline was subjected to diazo-coupling by adding to the reaction mixture 0.5 ml each of 0.04% sodium nitrite (0.48M hydrochloric acid solution), 0.3% ammonium sulfamate and 0.07% N-1-naphthylethylenediaminedihydrochloride in that order. Thereafter, absorbances were measured at 545 nm and the difference between those of each sample and blank was regarded as the reactivity. The results are shown in Table 1 (the difference is expressed by "Δ" in the table and also in other tables and figures).

TABLE 1

| Amount of aprotinin (mg) | Reactivity ($\Delta A_{545}$ nm/30 min) |
|---|---|
| 0 | >1.5 |
| 0.5 | 0.437 |
| 1.0 | 0.153 |
| 2.0 | 0.000 |
| 4.0 | 0.000 |
| 6.0 | 0.000 |

As is evident from Table 1, activation of factor G in the lysate reagent can be inhibited completely when 2.0 mg or more of aprotinin is added to 0.04 ml of the lysate reagent.

2) To 0.04 ml of the lysate reagent prepared in the above 1) were added 0.04 ml of 0.5M Tris-HCl/0.4M magnesium sulfate buffer (pH 8.0) containing 2.0, 4.0 or 6.0 mg of aprotinin, which completely inhibited factor G system reaction in the lysate reagent, and 0.02 ml of 4.0 mM Boc-Leu-Gly-Arg-pNA to obtain an aprotinin-containing lysate reagent. Separately, to 0.04 ml of the lysate reagent were added 0.04 ml of 0.5M Tris-HCl/0.4M magnesium sulfate buffer (pH 8.0) containing no aprotinin and 0.02 ml of 4.0 mM Boc-Leu-Gly-Arg-pNA. To each of these was added 0.1 ml of DW (blank) or Et derived from *Escherichia coli* 0111:B4 (Westphal type, available from Sigma; 6.25, 12.5, 25.0 or 50.0 pg/ml) as a sample. Thereafter, the reaction was effected in the same manner as described in the above 1) to prepare calibration curves of Et. The results are shown in FIG. 2.

Figure 2:
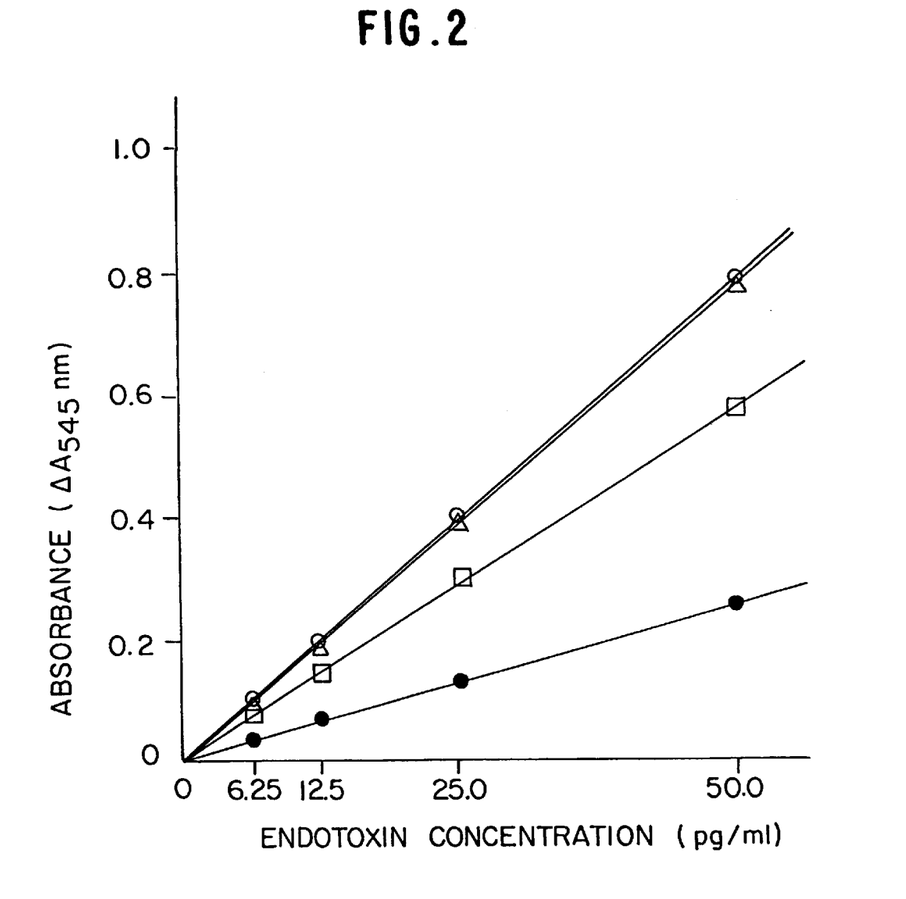
FIG. 2 is a graph showing results of Example 1–2) in which calibration curves are obtained by plotting absorbance against endotoxin concentration as a function of added amounts of aprotinin (- o -: not added, - Δ -: 2.0 mg, - □ -: 4.0 mg and - ● -: 6.0 mg).

It can be found from FIG. 2 that the reactivity with Et decreases as the amount of added aprotinin increases. By the use of these calibration curves, the amount of aprotinin which gives activity of the factor C system reaction in the lysate corresponding to the Et concentration in each sample can be selected.

Further, it is evident that Et assay can be effected using a limulus reagent which is prepared by adding aprotinin to a usual lysate reagent without influence of β-glucan.

Preparation of β-glucan

The method disclosed in WO90/02951 was followed. One gram of curdlan (available from Wako Pure Chemical Industries) was suspended in about 100 ml of a 5 mM NaOH aqueous solution and sonicated by Sonicator™ (Model 5202 PZT, manufactured by Ohtake Seisakusho, Tokyo) at 20 KHz and 80 W for 12 minutes under ice-cooling to degrade curdlan. The resulting solution was adjusted to give a final NaOH concentration of 0.3M with a 5M NaOH aqueous solution and subjected to a gel permeation chromatography (GPC columns, two TSK gel G3000PW$_{XL}$ and one G$^2$500PW$_{XL}$; mobile phase, 0.3M NaOH aqueous solution; flow rate, 0.5 ml/min). The resulting fractions were pooled and again subjected to the chromatography to collect a fraction of a molecular weight of 216,000, thereby obtaining a GPC-fractionation purified β-glucan preparation.

The thus obtained β-glucan preparation was also used in the following examples.

EXAMPLE 2
Et Assay Using a Reagent Prepared by Adding Aprotinin to Amebocyte Followed by Extraction A 1.0 liter portion of hemolymph of *T. tridentatus* was centrifuged at 1,500 rpm at 4° C. for 10 minutes and about 21 g of the resulting precipitate (amebocytes) was mixed with 210 ml of 0.02M Tris-HCl buffer (pH 8.0) containing 12 g of aprotinin and uniformly homogenized in Polytron R PT10 to effect extraction. The resulting homogenate was subjected to centrifugation at 10,000×G for 30 minutes while cooling to obtain 190 ml of a supernatant (aprotinin-containing lysate reagent).

To 0.04 ml of each of the thus obtained aprotinin-containing lysate reagent (invention) and a lysate reagent prepared in the same manner but without adding aprotinin (comparison) were added 0.01 ml of 2M Tris-HCl buffer (pH 8.0), 0.03 ml of 0.4M magnesium chloride and 0.02 ml of 3.0 mM Boc-Leu-Gly-Arg-pNA, followed by the addition of 0.1 ml of DW (blank), Et or β-glucan as a sample. Further, 0.05 ml each of Et and β-glucan having two-fold concentration were added as another sample. Each of the resulting mixtures was incubated at 37° C. for 30 minutes, the reaction was terminated with 0.4 ml of 0.8M acetic acid and then the thus formed p-nitroaniline was determined by measuring absorbance at 405 nm to compare reactivities. The results are shown in Table 2.

From the results, it is evident that Et assay can be effected using an aprotinin-containing lysate reagent prepared by adding aprotinin to a limulus hemolymph amebocyte prior to extraction without influence of β-glucan. In other words, it was confirmed that the factor G system reaction is substantially inhibited without inhibiting the factor C system reaction in the assaying system of the present invention.

TABLE 2

| | Reactivity ($\Delta A_{405}$ nm/30 min) | |
|---|---|---|
| Samples | Invention | Comparison |
| Et* | 0.317 | 0.344 |
| β-Glucan** | 0.000 | 0.183 |
| Et + β-glucan | 0.317 | 0.526 |

*Et concentration: 3.0 pg/0.1 ml sample
**β-glucan concentration: 5.0 pg/0.1 ml sample

EXAMPLE 3
Et Assay Using a Reagent Prepared by Dissolving a Lyophilized Lysate Reagent in an Aprotinin-Containing Solution One vial portion of "Pyrotel-T" (a lyophilized preparation of a lysate reagent prepared from *L. polyphemus* for a gelation method use, manufactured by Capecod and available from Seikagaku Corporation) was dissolved in 5.0 ml of DW in which 270 mg of aprotinin had been dissolved in advance (invention). Another one vial portion of the lyophilized limulus reagent preparation was dissolved in 5.0 ml of DW containing no aprotinin (comparison). A 0.1 ml aliquot of these solutions was dispensed in 0.1 ml portions into test tubes, followed by addition of 0.1 ml of DW (blank), Et or β-glucan as a sample. Further, 0.05 ml each of Et and β-glucan both having two-fold concentration were added as another sample. After gently mixing the reaction mixture, each test tube was arranged on an analysis module attached to a nephelometric analyzer (Toxinometer ET-201, available from Wako Pure Chemical Industries) and incubated at 37° C. for 60 minutes to record gelation time (Tg) and thereby to examine reactivity of the reagent of the present invention. The results are shown in Table 3.

From the results, it is evident that Et assay can be effected by adding aprotinin to a commercially available lyophilized lysate reagent (gelation method limulus test reagent) prior to the addition of samples without influence of β-glucan.

TABLE 3

| Sample | Reactivity (Tg, min) | |
|---|---|---|
| | Invention | Comparison |
| DW (blank) | >60 | >60 |
| Et* | 33.5 | 29.7 |
| β-Glucan** | >60 | 32.3 |
| Et + β-glucan | 33.3 | 19.6 |

*Et concentration: 2.0 pg/0.1 ml sample
**β-glucan concentration: 40.0 pg/0.1 ml sample

EXAMPLE 4
Et Assay Using a Reagent Prepared by Dissolving a Lyophilized Preparation Containing a Lysate Reagent and a Synthetic Substrate in an Aprotinin-Containing Solution One vial portion of "Toxicolor System LS-200 Set" (a lyophilized preparation containing a lysate reagent prepared from *T. tridentatus* and Boc-Leu-Gly-Arg-pNA for chromogenic synthetic substrate method use, manufactured by and available from Seikagaku Corporation) was dissolved in 2.8 ml of 0.2M Tris-HCl buffer (pH 8.0) in which 140 mg of aprotinin had been dissolved in advance to obtain a reagent of the present invention. Another one vial portion of the lyophilized preparation was dissolved in 2.8 ml of 0.2M Tris-HCl buffer (pH 8.0) containing no aprotinin to serve as a comparative reagent. To 0.1 ml of each of these solutions was added 0.1 ml of DW (blank), Et or β-glucan as a sample to be tested. Further, 0.05 ml each of Et and β-glucan both having two-fold concentration were added as another sample. Each of these mixtures was allowed to react in the same manner as described in Example 1-1) to evaluate reactivity of the reagent of the present invention. The results are shown in Table 4.

TABLE 4

| Sample | Reactivity $\Delta A_{545}$ nm/30 min) | |
|---|---|---|
| | Invention | Comparison |
| Et* | 0.863 | 0.891 |
| β-Glucan** | 0.000 | >1.5 |
| Et + β-glucan | 0.863 | >1.5 |

*Et concentration: 5.0 pg/0.1 ml sample
**β-glucan concentration: 50.0 ng/0.1 ml sample From the results, it is evident that Et assay can be effected by adding aprotinin to a commercially available chromogenic synthetic substrate method limulus test reagent (lyophilized preparation) prior to the addition of sample without influence of β-glucan.

EXAMPLE 5
Et Assay Using a Reagent Prepared by Adding Aprotinin to Amebocyte Followed by Extraction, Lyophilizing the Mixture and Dissolving it in a Solution A 2.0 ml portion of an aprotinin-containing lysate reagent prepared by adding aprotinin to amebocyte prior to extraction in the same manner as in Example 2 was mixed with 0.4 ml of 0.4M magnesium chloride followed by lyophilization to obtain a reagent for Et assay of the present invention. Also, 2.0 ml of an aprotinin-free lysate reagent prepared in the same manner as in Example 1-1) was mixed with 0.4 ml of 0.4M magnesium chloride followed by lyophilization to obtain a comparative reagent. Each of the thus lyophilized preparations was dissolved in 2.0 ml of DW. To 0.1 ml of each of these solutions was added 0.1 ml of DW (blank), Et or β-glucan as a sample. After gentle mixing, the mixture was statically incubated at 37° C. for 60 minutes and then the presence of gel formation was judged by the naked eye by slanting the tube at an angle of 180° to evaluate reactivity of the reagent of the present invention. The results are shown in Table 5. In the table, + means gel formation and means no gel formation.

TABLE 5

| Sample | Reactivity | |
|---|---|---|
| | Invention | Comparison |
| DW (blank) | – | – |
| Et* | + | + |
| β-Glucan** | – | + |

*Et concentration: 4.0 pg/0.1 ml sample
**β-glucan concentration: 40.0 ng/0.1 ml sample From the results, it is evident that Et assay can be effected by lyophilizing an aprotinin-containing lysate reagent prepared by adding aprotinin to amebocyte prior to extraction without influence of β-glucan.

EXAMPLE 6
Et Assay Using a Reagent Prepared by Dissolving in a Solution a Lyophilized Preparation Containing a Lysate Reagent, a Synthetic Substrate and Aprotinin Mixed were 2.0 ml of the aprotinin-free lysate reagent obtained in Example 1-1), 0.9 ml of 3.4 mM chromogenic synthetic substrate (Boc-Leu-Gly-Arg-pNA), 1.0 ml of 0.8M magnesium sulfate and 0.5 ml of aprotinin aqueous solution (240 mg/ml). The mixture was lyophilized to obtain a reagent for Et assay of the present invention. Also, a comparative reagent was prepared in the same manner except that 0.5 ml of DW was used in place of the aprotinin aqueous solution. Each of the thus obtained lyophilized preparations was dissolved in 5.0 ml of 0.2M Tris-HCl buffer (pH 8.0). To 0.1 ml of each of the resulting solutions was added 0.1 ml of DW (blank), Et or β-glucan as a sample. Further, 0.05 ml each of Et and β-glucan both having two-fold concentration were added as another sample. Each of these mixtures was allowed to react in the same manner as described in Example 1-1) to evaluate reactivity of the reagent of the present invention. The results are shown in Table 6.

TABLE 6

| Sample | Reactivity ($\Delta A_{545}$ nm/30 min) | |
|---|---|---|
| | Invention | Comparison |
| Et* | 0.669 | 0.697 |
| β-Glucan** | 0.000 | >1.5 |
| Et + β-glucan | 0.669 | >1.5 |

*Et concentration: 4.0 pg/0.1 ml sample
**β-glucan concentration: 40.0 ng/0.1 ml sample From the results, it is evident that Et assay can be effected by using a reagent prepared by lyophilizing a mixture containing a lysate reagent, a synthetic substrate and aprotinin without influence of β-glucan.

EXAMPLE 7
Et Assay in Which Aprotinin is Added in Advance to Samples

DW (blank), Et, β-glucan and a mixture of the same volume of Et and β-glucan both having two-fold concentration were prepared as samples to be tested. To 0.05 ml of each of these samples were added 0.05 ml of aprotinin aqueous solution (100 mg/ml) and then 0.1 ml of "Toxicolor System LS-200 Set" which had been dissolved in 2.8 ml of 0.2M Tris-HCl buffer (pH 8.0). Thereafter, each of the thus prepared mixtures was allowed to react in the same manner as described in Example 1-1). The same procedure was repeated except that the same volume of DW was used in place of the aprotinin aqueous solution in order to compare their reactivities. The results are shown in Table 7.

TABLE 7

| | Reactivity ($\Delta A_{545}$ mn/30 min) | |
|---|---|---|
| Sample | Aprotinin added | Aprotinin not added |
| Et* | 0.883 | 0.928 |
| β-Glucan** | 0.000 | >1.5 |
| Et + β-glucan | 0.885 | >1.5 |

*Et concentration: 5.0 pg/0.05 ml sample
**β-glucan concentration: 30.0 ng/0.05 ml sample From the results, it is evident that Et assay can be effected by adding aprotinin in advance to samples without influence of β-glucan.

EXAMPLE 8
Et Assay in Which a Sample is Added to a Lysate Reagent and Immediately Thereafter Aprotinin is Added Thereto One vial portion of "Pyrotel" (a lyophilized preparation of a lysate reagent prepared from *L. polyphemus* for a gelation method use, manufactured by Capecod and available from Seikagaku Corporation) was dissolved in 5.0 ml of DW. The thus prepared solution was dispensed into test tubes in 0.1 ml portions under ice-cooling and 0.05 ml of DW (blank), Et or β-glucan was added thereto as a sample. Immediately thereafter, 0.05 ml of an aprotinin aqueous solution (110 mg/ml) was added to the respective test tubes. After gentle mixing, each of these mixtures was incubated statically at 37° C. for 60 minutes to judge the presence of gel formation in the same manner as described in Example 5. The same procedure was repeated except that the same volume of DW was used in place of the aprotinin aqueous solution in order to compare their reactivities. The results are shown in Table 8.

TABLE 8

| | Reactivity | |
|---|---|---|
| Sample | Aprotinin added | Aprotinin not added |
| DW (blank) | − | − |
| Et* | + | + |
| β-Glucan** | − | + |

*Et concentration: 2.0 pg/0.05 ml sample
**β-glucan concentration: 20.0 ng/0.05 ml sample From the results, it is evident that Et assay can be effected by adding samples to a lysate reagent and immediately thereafter adding aprotinin thereto without influence of β-glucan.

EXAMPLE 9
Et Assay in Which Aprotinin is Added to Serine Protease-Containing Samples A 0.01 ml portion of DW or Et solution (400 pg/ml) was added to 0.01 ml of a 100 μg/ml solution of trypsin (derived from bovine pancreas, manufactured by Miles Laboratories and available from Seikagaku Corporation) or DW, and 0.08 ml of an aprotinin aqueous solution (5.0 mg/ml) was added thereto followed by mixing. Each of the thus prepared mixtures was further mixed with 0.1 ml of a limulus test reagent for Et-specific chromogenic synthetic substrate method use (Endospecy, available from Seikagaku Corporation) and subjected to the same reaction as described in Example 1-1) to determine recovery of Et added to the trypsin sample. The same procedure was repeated except that 0.08 ml of DW was used in place of the aprotinin aqueous solution. The results are shown in Table 9.

TABLE 9

| Sample | Addition of aprotinin to samples | Et added ($A_{545}$ nm) | Et not added ($A_{545}$ nm) | $\Delta A_{545}$ nm | Recovery of Et (%) |
|---|---|---|---|---|---|
| DW | yes | 0.729 | 0.070 | 0.659 | 100 |
| Trypsin | yes | 0.743 | 0.095 | 0.648 | 98.3 |
| DW | no | 0.701 | 0.031 | 0.670 | 100 |
| Trypsin | no | >1.5 | >1.5 | — | — |

As is evident from the results shown in Table 9, Et in a trypsin-containing sample can be assayed accurately by a limulus test by adding aprotinin to the trypsin-containing sample in advance.

EXAMPLE 10
Et Assay of Serine Protease-Containing Samples in Which Aprotinin is Added to a Lysate Reagent A 0.08 ml portion of an aprotinin aqueous solution (8 mg/ml) was added to 0.1 ml of Toxicolor System LS-200 Set followed by mixing. To this was added 0.02 ml of a solution prepared by mixing a 10 units/ml solution of thrombin (derived from bovine serum, available from Sigma) or DW with the same volume of Et solution (400 pg/ml). Each of the thus prepared mixtures was subjected to the same reaction as described in Example 1-1) to determine recovery of Et added to the thrombin sample. The same procedure was repeated except that 0.08 ml of DW was used in place of the aprotinin aqueous solution. The results are shown in Table 10.

TABLE 10

| Sample | Addition of aprotinin to lysate reagent | Et added ($A_{545}$ nm) | Et not added ($A_{545}$ nm) | $\Delta A_{545}$ nm | Recovery of Et (%) |
|---|---|---|---|---|---|
| DW | yes | 0.718 | 0.068 | 0.650 | 100 |
| Thrombin | yes | 0.764 | 0.116 | 0.648 | 99.7 |
| DW | no | 0.693 | 0.028 | 0.665 | 100 |
| Thrombin | no | >1.5 | >1.5 | — | — |

As is evident from the results shown in Table 10, Et in a thrombin-containing sample can be assayed accurately by adding aprotinin to a limulus test reagent.

EXAMPLE 11
Et Assay in Which Serine Protease-Containing Samples are Pretreated With an Aprotinin-Immolized Insoluble Carrier Prior to Limulus Test A 10 ml portion of a 200 μg/ml solution of trypsin (derived from swine pancreas, manufactured by Sigma) was applied to a column (1.2×4.0 cm) packed with Et-free aprotinin-immobilized cellulofine (prepared by the method described below) which had been equilibrated with 0.1M Tris-HCl buffer (pH 8.0) containing 0.15M NaCl. The column was then washed with 0.1M Tris-HCl buffer (pH 8.0) containing 0.15M NaCl, and fractions passed through the column were pooled. To 0.1 ml of the pooled fraction or 0.1 ml of DW was added 0.01 ml of an Et solution (400 pg/ml) and subsequently 0.1 ml of Endospecy. The resulting mixture was allowed to react in the same manner as in Example 1-1) to determine recovery of Et in the fraction. The same procedure was repeated except that 0.01 ml of DW or an Et solution and subsequently 0.1 ml of Endospecy were added to 0.1 ml of untreated trypsin solution. The results are shown in Table Table 11.

TABLE 11

| Sample | Et added ($A_{545}$ nm) | Et not added ($A_{545}$ nm) | $\Delta A_{545}$ nm | Recovery of Et (%) |
|---|---|---|---|---|
| DW | 0.709 | 0.032 | 0.677 | 100 |
| Passed-through fraction | 0.710 | 0.034 | 0.676 | 99.9 |
| Untreated trypsin | >1.5 | >1.5 | — | — |

As is evident from the results shown in Table 11, Et in a trypsin-containing sample can be assayed accurately by limulus test when trypsin is allowed to contact in advance with an aprotinin-immobilized insoluble carrier.

Preparation of Aprotinin-Immobilized Cellulofine

A 10 g portion of Formyl-Cellulofine (manufactured by Chisso and available from Seikagaku Corporation) was washed thoroughly with 0.1M phosphate-Na buffer (pH 7.1), suspended in 20 ml of an aprotinin solution (20 mg/ml in 0.1M phosphate-Na buffer, pH 7.1). Fifty mg of NaC-NBH$_3$ was added to the suspension. After gently stirring at room temperature for 8 hours, the suspension was washed with 0.2M Tris-HCl buffer (pH 7.0) and filtered. Five ml of the above buffer containing 10 mg of NaCNBH$_3$ was added to the resulting residue followed by shaking at room temperature for 3 hours. Thereafter, the thus obtained suspension was washed thoroughly with 0.1M Tris-HCl buffer (pH 8.0) containing 0.15M NaCl.

EXAMPLE 12

The procedure of Example 2 was repeated except for using as a sample 0.1 ml of platelet rich plasma obtained from a patient who was suspected to suffer from complicated sepsis which was treated with perchloric acid according to the method described in U.S. Pat. No. 4,495,294 and then neutralized. The sample was also cultured according to the usual method to detect microbial infection. As a result, a number of *E. coli* colonies were detected in conformity with the quantitative reactivity of Et.

Also, effectiveness of the reagent or method of the present invention was confirmed when the same sample was tested in accordance with the procedures of Examples 3 to 8.

Thus, the reagent for Et assay can be prepared by such a simple and economical manner that a lysate reagent is combined with aprotinin. It is especially useful for assaying clinical samples from patients who are suspected to suffer from infectious diseases or sepsis, which are not proved to contain endotoxin, and it can accurately judge true Gram negative bacterial infection (endotoxemia). In addition, the present invention is also advantageous in that endotoxin contained in various serine protease-containing samples can be assayed easily and accurately, whereas such samples cannot be assayed by the conventional limulus test or need to be subjected to complicated pretreatment because serine proteases strongly interfere the limulus reaction.

While the invention has been described in detail and with reference to specific examples thereof, it will be apparent to one skilled in the art that various changes and modifications can be made therein without departing from the spirit and scope thereof.

What is claimed is:

1. A reagent composition for specifically assaying for endotoxin in a sample comprising:

(A) aprotinin; and (B) a horseshoe crab amebocyte lysate reagent, wherein said aprotinin is present in the reagent composition in an amount sufficient to completely inhibit activation of factor G present in the horseshoe crab amebocyte lysate reagent.

2. A kit for specifically assaying for endotoxin in a sample comprising:

(A) a horseshoe crab amebocyte lysate reagent; and (B) a reagent containing aprotinin in an amount sufficient to completely inhibit activation of factor G present in the horseshoe crab amebocyte lysate reagent.

3. The kit as claimed in claim 2, wherein said reagent (B) comprises a buffer agent.

4. The kit as claimed in claim 2, wherein said lysate reagent is lyophilized, and said kit includes a solution for dissolving said lyophilized lysate reagent.

5. The kit as claimed in claim 2, wherein said reagent (B) is lyophilized, and said kit includes a solution for dissolving said lyophilized reagent (B).

6. The kit as claimed in claim 2, wherein said kit additionally comprises a lyophilized standard endotoxin, and a solution for dissolving said lyophilized standard endotoxin.

* * * * *